US012653064B2

(12) United States Patent
To et al.

(10) Patent No.: US 12,653,064 B2
(45) Date of Patent: Jun. 9, 2026

(54) POLYCHLOROTRIFLUOROETHYLENE (PCTFE) POLYMER ENCLOSURE FOR AN IMPLANTABLE DEVICE

(71) Applicant: Neuralink Corp., Fremont, CA (US)

(72) Inventors: John W.F. To, Castro Valley, CA (US); Ik Soo Kwon, San Francisco, CA (US); Dongjin Seo, San Francisco, CA (US); Yu Niu (Peter) Huang, Alameda, CA (US); Jiahao Guo, San Mateo, CA (US); Robin E. Young, San Francisco, CA (US); Joshua Scott Hess, Dublin, CA (US); Zachary M. Tedoff, Oakland, CA (US); Russell N. Ohnemus, San Francisco, CA (US); Dominic A. Herincx, San Mateo, CA (US)

(73) Assignee: Neuralink Corp., Fremont, CA (US)

( * ) Notice: Subject to any disclaimer, the term of this patent is extended or adjusted under 35 U.S.C. 154(b) by 1240 days.

(21) Appl. No.: 17/529,217

(22) Filed: Nov. 17, 2021

(65) Prior Publication Data

US 2023/0154809 A1    May 18, 2023

(51) Int. Cl.
*A61B 5/293* (2021.01)
*A61B 5/271* (2021.01)
(Continued)

(52) U.S. Cl.
CPC ............. *H10W 76/18* (2026.01); *A61B 5/271* (2021.01); *A61B 5/293* (2021.01); *A61F 2/82* (2013.01);
(Continued)

(58) Field of Classification Search
CPC ..... H01L 23/08; H01L 21/52; A61N 1/37514; A61B 5/293; A61B 5/271; A61F 2/82; H01B 3/306
See application file for complete search history.

(56) References Cited

U.S. PATENT DOCUMENTS 10,137,303 B2 * 11/2018 Greenberg ......... A61N 1/36082
11,107,703 B2    8/2021 Tolosa et al.
(Continued)

FOREIGN PATENT DOCUMENTS

CN    103079638 B  *  5/2015  ............... A61N 1/36
CN    111632267 A  *  9/2020  ............. B33Y 50/02

OTHER PUBLICATIONS

Translation CN 111632267 (Year: 2020).*
Translation CN 103079638 (Year: 2015).*

*Primary Examiner* — Adam Z Minchella
(74) *Attorney, Agent, or Firm* — Oblon, McClelland, Maier & Neustadt, L.L.P.

(57) ABSTRACT

An implantable device and method of manufacture include a substantially hermetic polychlorotrifluoroethylene (PCTFE) enclosure with closely-spaced wires extending out of the enclosure. The implantable device includes a PCTFE first portion of an enclosure and a PCTFE second portion of the enclosure. The first and second portions are configured to mate with each other to form the enclosure. A plurality of insulated wires extend between the first and second portions of the enclosure. Each of the insulated wires are parallel to each other and separated by less than 150 micrometers ($\mu$m) from a neighboring wire. A thermal weld seam of PCTFE is disposed between the first portion of the enclosure and the second portion of the enclosure and conformally adheres around insulation of each wire such that the enclosure is sealed.

14 Claims, 13 Drawing Sheets

(51) Int. Cl.

| | | |
|---|---|---|
| *A61F 2/82* | (2013.01) | |
| *A61N 1/375* | (2006.01) | |
| *H01B 3/30* | (2006.01) | |
| *H10W 72/00* | (2026.01) | |
| *H10W 76/18* | (2026.01) | |

(52) U.S. Cl.
CPC ......... *A61N 1/37514* (2017.08); *H01B 3/306* (2013.01); *H10W 72/071* (2026.01)

(56)                           References Cited

U.S. PATENT DOCUMENTS

| | | | |
|---|---|---|---|
| 11,444,056 B2 | 9/2022 | Chen et al. | |
| 2003/0120320 A1* | 6/2003 | Solom ..................... | H01G 9/008 |
| | | | 607/36 |
| 2005/0070982 A1* | 3/2005 | Heruth ................. | A61N 1/0553 |
| | | | 607/119 |
| 2011/0238145 A1* | 9/2011 | Swanson .............. | A61N 1/0551 |
| | | | 607/116 |
| 2013/0144365 A1* | 6/2013 | Kipke ................. | A61B 5/4064 |
| | | | 607/148 |
| 2018/0296243 A1 | 10/2018 | Hanson et al. | |
| 2020/0086111 A1 | 3/2020 | Young et al. | |

* cited by examiner

200

210                                                             204

208                              208        206

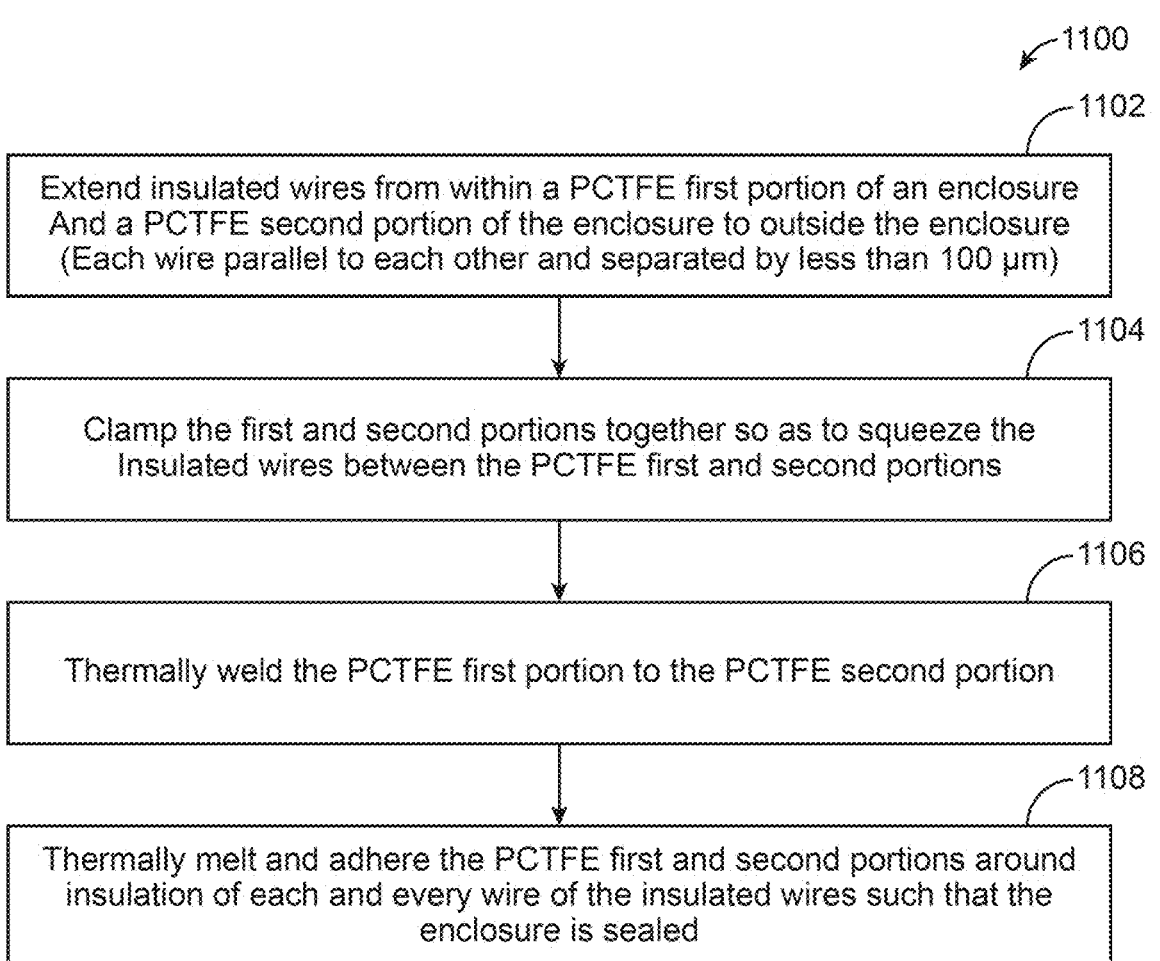

1100

1102

Extend insulated wires from within a PCTFE first portion of an enclosure
And a PCTFE second portion of the enclosure to outside the enclosure
(Each wire parallel to each other and separated by less than 100 μm)

1104

Clamp the first and second portions together so as to squeeze the
Insulated wires between the PCTFE first and second portions

1106

Thermally weld the PCTFE first portion to the PCTFE second portion

1108

Thermally melt and adhere the PCTFE first and second portions around
insulation of each and every wire of the insulated wires such that the
enclosure is sealed

FIG. 11

POLYCHLOROTRIFLUOROETHYLENE (PCTFE) POLYMER ENCLOSURE FOR AN IMPLANTABLE DEVICE

CROSS-REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

BACKGROUND OF THE INVENTION

Implantable devices are used for a variety of applications such as cardiac pacemakers, cochlear implants, and recording and stimulating electrical signals in target biological tissue. In many cases, active electronic devices are critical to the functionality of the implantable device. Body environments such as brain tissue, heart tissue, and the like have high humidity and bodily fluids. Implantable devices are generally in an in-vivo environment including high humidity and oxidative inflammatory response that will put stress on sensitive components such as active electronics without proper protection. As a result, implantable devices generally have a rigid hermetic housing to protect the active electronics from environmental and mechanical stress. Such housings are commonly manufactured from glass or metal, which are suitable for a variety of applications due to the hermetic nature of these materials.

As implantable devices advance, it is increasingly common to have a large number of wires extending from the implantable device. For example, a brain-machine interface includes thousands of wires extending from an implantable device and implanted in a brain. In such applications, with a large number of tightly spaced wires extending through the housing, problems arise that make traditional housing materials less suitable for these applications. For example, a glass housing can crack or otherwise fail if manufactured with tightly spaced wires extending through the glass.

BRIEF SUMMARY OF THE INVENTION

In some embodiments, an implantable device includes a polychlorotrifluoroethylene (PCTFE) first portion of an enclosure, a PCTFE second portion of the enclosure, the first and second portions configured to mate with each other to form the enclosure. The implantable device includes a plurality of insulated wires, each wire of the plurality of insulated wires parallel to each other and separated by less than 150 micrometers (μm) from a neighboring wire of the plurality of insulated wires, the plurality of insulated wires extending between the first and second portions of the enclosure. The implantable device includes a thermal weld seam of PCTFE disposed between the first portion of the enclosure and the second portion of the enclosure and conformally adhering around insulation of each and every wire of the plurality of insulated wires such that the enclosure is sealed.

In some aspects, insulation of each of the plurality of insulated wires is composed of polyimide. In some aspects, each wire of the plurality of insulated wires has a rectangular cross section, having been produced by lithography. In some aspects, the plurality of insulated wires comprises at least 500 wires. In some aspects, each wire of the plurality of insulated wires includes a plurality of metal traces terminating in a respective plurality of electrodes.

In some aspects, each wire of the plurality of insulated wires is separated by between 10 micrometers (μm) and 50 micrometers (μm) from a neighboring wire. In some aspects, the electrodes are implanted in a brain. In some aspects, the implantable device further includes a volume disposed between the first portion of the enclosure and the second portion of the enclosure and an integrated circuit sealed within the volume. In some aspects, the implantable device further includes a volume disposed between the first portion of the enclosure and the second portion of the enclosure and a wireless charging device sealed within the volume.

In some embodiments, a method for manufacturing an implantable device includes extending a plurality of insulated wires from within a polychlorotrifluoroethylene (PCTFE) first portion of an enclosure and a PCTFE second portion of the enclosure to outside the enclosure, each wire of the plurality of insulated wires parallel to each other and separated by less than 150 micrometers (μm) from a neighboring wire of the plurality of insulated wires, clamping the first and second portions together so as to squeeze the plurality of insulated wires between the PCTFE first and second portions, thermally welding the PCTFE first portion to the PCTFE second portion, and thermally melting and adhering the PCTFE first and second portions around insulation of each and every wire of the plurality of insulated wires such that the enclosure is sealed.

In some aspects, insulation of each of the plurality of insulated wires is composed of polyimide. In some aspects, each wire of the plurality of insulated wires has a rectangular cross section, having been produced by lithography. In some aspects, the thermal welding includes heating the PCTFE portions and the plurality of insulated wires to a temperature between 200 degrees Celsius (C) and 300 degrees Celsius (C). In some aspects, the method further includes inserting the PCTFE first portion into an insert disposed in a base, wherein the thermal welding is performed using a heater disposed below the base.

In some aspects, the clamping includes applying pressure to the PCTFE first portion using a first piston and applying pressure to the PCTFE second portion using a second piston. In some aspects, the pressure applied to the first piston is between 275,790 Pascals (Pa) (40 pounds per square inch (psi)) and 551,581 Pa (80 psi) and the pressure applied to the second piston is greater than 100 psi. In some aspects, the pressure applied to the first piston is different from the pressure applied to the second piston.

In some aspects, the method further includes, before extending the plurality of probes between the PCTFE first portion and the PCTFE second portion, sonicating the PCTFE first portion and heating the PCTFE first portion. In some aspects, the thermal welding is performed by a sealing system, the method further comprising, before the thermal welding, warming the sealing system to at least 15 degrees Celsius (C).

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

FIG. 11 is an example flowchart describing a method of manufacturing an implantable device, according to aspects of the present disclosure.

DETAILED DESCRIPTION OF THE INVENTION

Figure 1A:
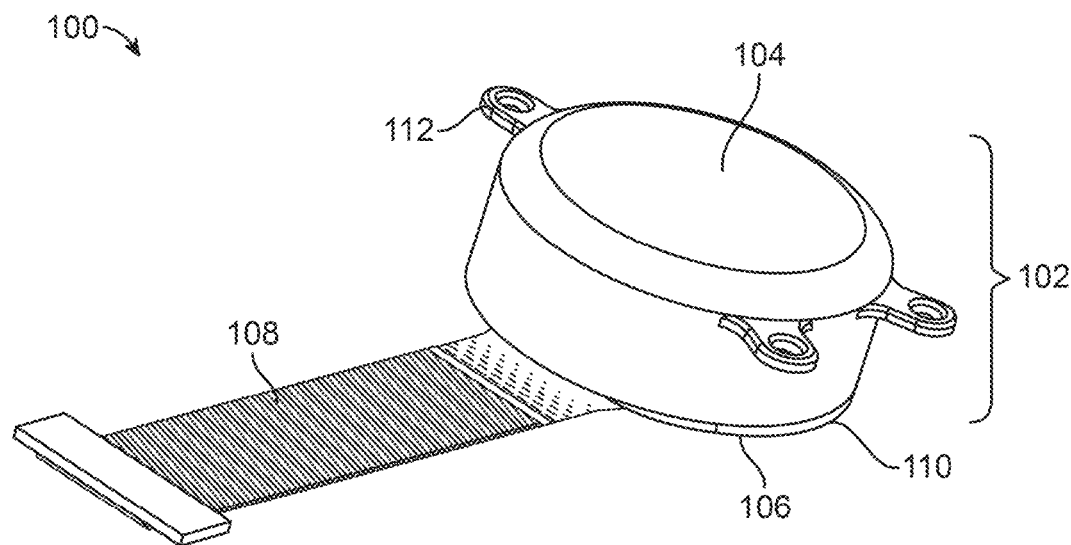
FIG. 1A illustrates an implantable device with a PCTFE enclosure, according to an aspect of the present disclosure.

The present disclosure relates to systems and methods of manufacturing an implantable device with an enclosure composed of PCTFE. PCTFE can be sealed substantially hermetically around wires insulated with certain polymers, even when the wires are densely packed together. For example, a PCTFE enclosure can provide a substantially hermetic seal while being bonded around hundreds or thousands of insulated wires spaced apart closely, on the order of micrometers (μm).

As noted above, conventional enclosure materials suffer from several limitations. Implantable devices are traditionally enclosed using materials such as glass, titanium, or ceramic. These materials are generally well-suited as they fit the bill for creating a hermetic or substantially hermetic environment within the enclosure, as well as being biocompatible (e.g., not cytotoxic). However, as implantable devices evolve, so do the needs for the enclosure. In particular, devices are increasingly developed with large numbers of electrodes extending from the enclosure into tissue. For example, a brain-machine interface (BMI) uses multiple electrodes to stimulate brain tissue and record neurological signals. BMIs have the potential to help people with a wide range of clinical disorders, and have been applied in contexts such as neuroprosthetic control of computer cursors, robotic limbs, and speech synthesizers. Development of BMIs has been limited historically by an inability to record from large numbers of neurons. Due to recent developments in electrode fabrication, robotic insertion, electronic design, and signal processing, there is now the ability to implant a BMI with thousands of electrodes. This new generation of BMIs can include thousands of wires spaced relatively closely together (e.g., micron-level spacing) and connected to sensitive electronics. However, this means that traditional enclosure approaches are no longer feasible. Rigid materials such as glass may crack when manufactured with tightly-spaced openings to accommodate thousands of channels.

Techniques described herein address these issues. An enclosure is composed of PCTFE. PCTFE has been found to accommodate a large number of tightly-spaced wires while maintaining a substantially hermetic seal when manufactured with insulated wires under specific temperature and pressure conditions. The present disclosure provides a PCTFE enclosure design and manufacture process.

Many of the details, dimensions, angles and other features shown in the Figures are merely illustrative of particular embodiments. Accordingly, other embodiments can include other details, dimensions, angles and features without departing from the spirit or scope of the present invention. Various embodiments of the present technology can also include structures other than those shown in the Figures and are expressly not limited to the structures shown in the Figures. Moreover, the various elements and features shown in the Figures may not be drawn to scale. In the Figures, identical reference numbers identify identical or at least generally similar elements.

As used herein, the singular forms "a", "an", and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

Spatially relative terms, such as "beneath", "below", "lower", "above", "upper", and the like, may be used herein for ease of description to describe one element or feature's relationship to another element(s) or feature(s) as shown in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below, depending on the context of its use. The device may be otherwise oriented (rotated 90 degrees or at other orientations) and the spatially relative descriptors used herein are interpreted accordingly.

Although the terms "first", "second", etc. may be used herein to describe various elements, components, regions, layers and/or sections, it should be understood that they should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

As used herein, the terms "and/or" and "at least one of" include any and all combinations of one or more of the associated listed items.

As used herein, the terms "approximately" and "about" are used to provide flexibility to a numerical range endpoint by providing that a given value may be within a functional range greater than or less than the given value. As used herein, unless otherwise specified, the given value modified by approximately or about is modified by ±10%.

Device with Pctfe Enclosure

Figure 1B:
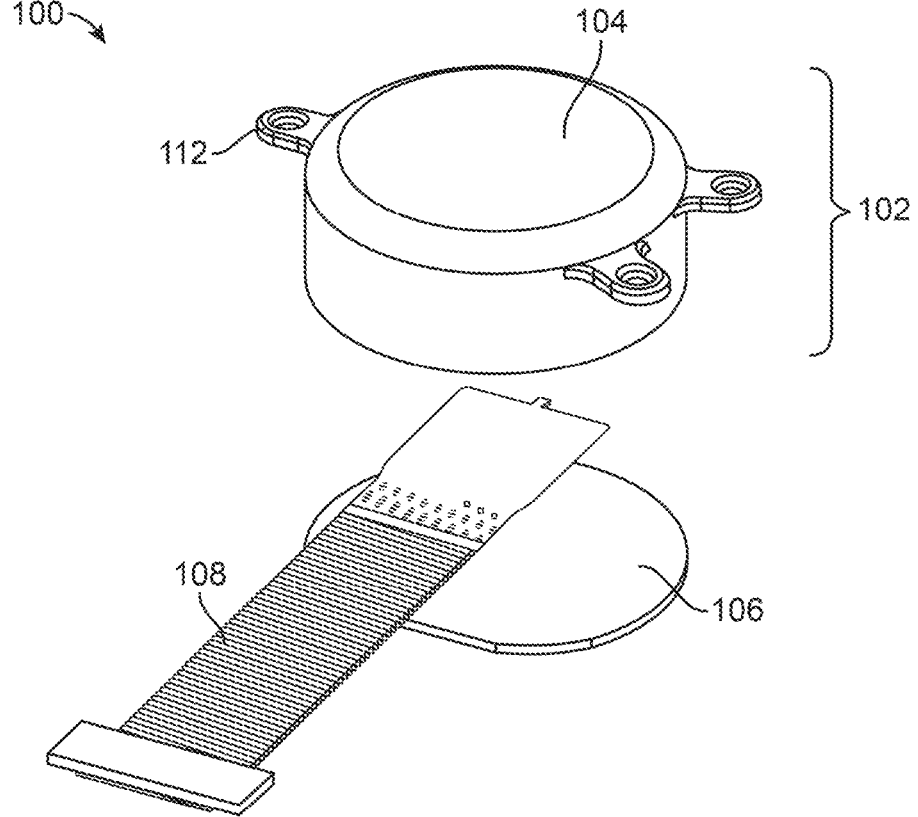
FIG. 1B is an exploded view of the implantable device of FIG. 1A.

FIGS. 1A and 1B illustrate an implantable device 100 according to some embodiments. FIG. 1A is a perspective view of the implantable device 100. FIG. 1B is an exploded view of implantable device 100. The implantable device 100 includes an enclosure 102. The enclosure 102 includes a first portion 104 and a second portion 106. Insulated wires 108 extend between the first portion 104 and the second portion 106.

In some embodiments, the first portion 104 and the second portion 106 are composed of polychlorotrifluoroethylene (PCTFE). The portions 104 and 106 of the enclosure 102 are hereafter referred to as a PCTFE first portion 104 and a PCTFE second portion 106. PCTFE is a polymer, specifically, a thermoplastic chloro-fluoropolymer with the molecular formula $(CF_2—CFCl)_n$, where n is the number of monomer units in the polymer molecule. PCTFE is similar to polytetrafluoroethylene (PTFE), except that PCTFE is a homopolymer of the monomer chlorotrifluoroethylene (CTFE) instead of tetrafluoroethene. PCTFE is manufactured and sold under trade names including KelF®, FluoroPro™, Neoflon®, and Aclar®. CTFE has similar properties to PCTFE and may be used as the enclosure 102 material alternatively or additionally.

In some embodiments, the implantable device 100 may include a volume holding circuitry, which can have variable shapes and sizes, and can be configured to remain in vivo within a subject following surgery. The implantable device can be, for example, disposed within a skull. The implantable device can further include a communications relay to transmit and receive signals to and from the implantable device. In some aspects, the implantable device can further include a wireless communications port, including an antenna configured to transmit radio frequencies, Wi-Fi frequencies, or the like, in order to relay data, electricity (e.g. for charging the probe device), or other signals.

Active electronic devices are critical components to the functionality of implantable medical devices, as without the electronic components, an active implantable medical device would not be able to perform as designed. The enclosure should be substantially hermetic to protect the active electronics from contacting the body environment, which can have high moisture, humidity, and oxidative properties. A hermetic enclosure will completely prevent the passage of liquids or gases. A substantially hermetic enclosure will prevent the passage of liquids or gases for a time on the order of years. For example, certain polymers may allow a small amount of gas or liquid to pass through after tens of years, which would be considered substantially hermetic.

PCTFE has several properties that are desirable for use in an implantable device. The physical properties and chemical properties of PCTFE allow it to be stable to withstand the harsh environment in-vivo, including high humidity and oxidative inflammatory biological response. PCTFE has good chemical resistance. Due to its high fluorine content and lack of hydrogen atoms, PCTFE is resistant to the attack by most chemicals and oxidizing agents. PCTFE also provides the rigidity needed to prevent mechanical stress on the implantable device, particularly on active electronics enclosed by the enclosure. Furthermore, PCTFE has a low dielectric constant that allows Bluetooth Low Energy (BLE) communication and makes wireless charging possible.

Another advantageous aspect about PCTFE is its barrier properties. PCTFE is substantially hermetic. PCTFE has a close to zero water absorption value of <0.01% (ISO 62). PCTFE also processes low water vapor permeability. PCTFE is a fluororesin with the highest gas barrier property with a WVTR (0.005 g/m2/24 hr) at 25° C. These properties are ideal for development of a substantially hermetic package.

PCTFE also processes several desirable mechanical properties and thermal properties. PCTFE has high tensile strength (ASTM D1708: 47 MPa), and moderate hardness (ASTM D638 Shore D 80). PCTFE has a melting point of 212° C. and a maximum temperature for continuous use of 120° C.). PCTFE also has glass transition temperature of 45° C. and good melt flow properties with excellent stress crack resistance. These properties make PCTFE suitable for compression molding, injection molding, precision molding and machining into desired shapes and parts and are ideal for a thermocompression bonding process. The mass flow properties of PCTFE allow it to reflow and fuse with itself at temperature above its melting point. The sealing steps described herein allow the first and second portions of the PCTFE enclosure to fuse around insulated wires following a thermocompression bonding.

Alternatively, or additionally, the first portion 104 and the second portion 106 are composed of other materials that have similar thermocompression properties to PCTFE such that the material can undergo thermocompression bonding using the techniques described herein. Examples of suitable materials include Liquid Crystal Polymer (LCP), High-Density Polyethylene (HDPE), Polytetrafluoroethylene (PTFE), Polyvinylidene fluoride (PVDF), Polyvinylidene Chloride (PVDC), and Ethylene Vinyl Alcohol (EVOH), all of which are biocompatible and suitable for implantation. Alternatively, or additionally, the first portion can be composed of Polyacrylonitrile (PAN), which also has similar thermocompression properties to PCTFE.

As shown in FIG. 1A, the first PCTFE portion 104 and the second PCTFE portion 106 are fused together to form the enclosure 102. A welded seam 110 seals the first PCTFE portion 104 and the second PCTFE portion 106 to form the enclosure 102. The welded seam 110 is further sealed around the insulated wires 108, with the insulated wires 108 extending between the first PCTFE portion 104 of the enclosure and the second PCTFE portion 106 of the enclosure. In some embodiments, at least 500 insulated wires 108 are included in the implantable device 100. In some embodiments, more than 1,000 wires 108 extend between the PCTFE portions 104 and 106. In some implementations, each of the insulated wires 108 are parallel to each other.

In some implementations, one or both of the PCTFE portions (e.g., the first PCTFE portion 104, as depicted in FIGS. 1A and 1B) includes an attachment means 112 to attach the implantable device 100 to a subject for implantation. In the example shown in FIGS. 1A and 1B, three attachment means 112 are included, in the form of three screw holes for attaching the implantable device 100 to a subject. For example, the implantable device can be disposed on a skull of a subject, and screws can be inserted through the attachment means 112 to hold the implantable device 100 in place near the skull of the subject. In some implementations, the screw holes are configured to hold screws with a diameter of about a millimeter (mm). For example, the screw holes may be about 1.8-1.9 mm in diameter, and biocompatible screws of about 1.8 mm in diameter are used for implantation. The PCTFE portions 104 and 106 may include one or more flat surfaces. The shape of the second PCTFE portion 106 may be substantially circular, as is shown in FIG. 1. In some implementations, one side of the second PCTFE portion 106 is flattened off so that the second PCTFE portion 106 is semicircular, as shown in FIG. 1. The first PCTFE portion 104 may have a similar profile, e.g., be cylindrical with a circular surface for coupling to the second PCTFE portion 106. In other implementations, the PCTFE portions may have other suitable shapes, such as square, rectangular, triangular, etc.

Figure 2:
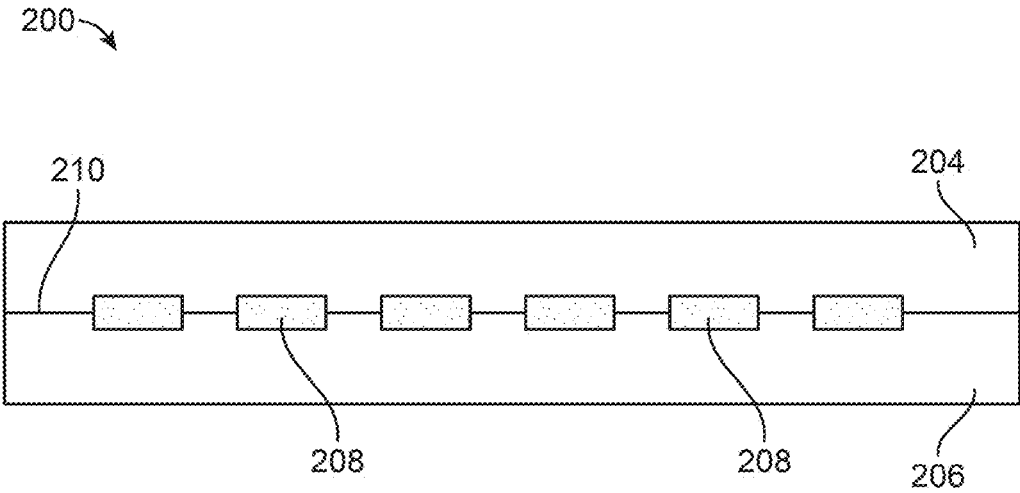
FIG. 2 illustrates a view of a PCTFE enclosure with insulated wires, according to an aspect of the present disclosure.

FIG. 2 illustrates a close-up cross-sectional view of a PCTFE enclosure 200 with insulated wires 208, according to an aspect of the present disclosure. The PCTFE enclosure 200 includes a first PCTFE portion 204 and a second PCTFE portion 206. The PCTFE portions 204 and 206 are fused together and around multiple insulated wires 208. A welded seam 210 joins the PCTFE portions 204 and 206 together between each of the insulated wires 208. In some embodiments, the welded seam 210 is a thermal weld seam of PCTFE. The welded seam 210 is disposed between the first PCTFE portion 204 of the enclosure and the second PCTFE portion 206 of the enclosure. The seam 210 conformally adheres around insulation of each and every wire of the plurality of insulated wires 208 such that the enclosure is sealed. The seam 210 conformally adheres around the insulation of the wires if the PCTFE portions are substantially hermetically sealed around the insulation of the wires. As noted above, a seal can be considered substantially hermetic if the seal prevent the passage of liquids or gases for a time on the order of years.

In some embodiments, the insulation of the insulated wires 208 is composed of a polymeric material that is biocompatible, bioimplantable, and can be welded to adhere to the PCTFE. For example, an insulation composed of polyimide (PI) has been found to conform well with PCTFE to seal the enclosure. In some implementations, polyimide thin film is the insulation material. As other examples, the insulation may include epoxy, polyparaxylylene, parylene, and/or acrylic. The insulated wires 208 are long and thin. For example, the insulated wires 208 each have a width from 5 μm to 50 μm, a nominal thickness from 4 μm to 6 μm, and a length of approximately 20 mm (e.g., between 15 mm and 25 mm). The thin dimensions and flexibility of insulated wires 208 provide improved biocompatibility, and can minimize tissue displacement in the target.

As shown in FIG. 2, each of the insulated wires 208 has a rectangular cross section. In some aspects, the insulated wires 208 are substantially rectangular in shape. The insulated wires 208 may be in the form of a thin film array composed of electrode contacts and metal traces. The insulated wires 208 may further include a sensor area where the thin film interfaces with custom chips that enable signal amplification and acquisition. A wafer-level microfabrication process may be used to achieve high-throughput manufacturing. For example, ten thin film arrays may be patterned on a single wafer, with 1,088 electrode contacts per thin film array.

In some implementations, the insulated wires 208 are produced by lithography. For example, integrated circuit chips are bonded to contacts on the sensor area of the thin film using a flip-chip bonding process. This approach provides the technical advantage of maintaining a small cross-sectional area, in order to minimize tissue displacement in the brain. To achieve this, while keeping channel count high, stepper lithography and other microfabrication techniques may be used to form the metal film at sub-micron resolution.

Manufacturing the insulated wires may include forming registration marks to allow for layer to layer alignment at a high resolution (e.g., at a resolution of approximately 40 nanometers (nm)). For example, silicon wafers are coated with photoresist 1201 (e.g., 1200 nm Deep UV (DUV)). The coated silicon wafers are exposed in a stepper lithography tool with primary mark (PM) reticle 1203. The coated silicon wafers are post-exposure baked (PEB) to develop photoresist 1205. The coated silicon wafers 1207 are UV baked and etched to a suitable depth (e.g., 120 nm) in the surface using Reactive Ion Etcher (RIE). The photoresist may then be stripped and stripping the photoresist using oxygen plasma.

Manufacturing the insulated wires may further include depositing a thin layer of biocompatible polymeric material such as PI. Metal traces may be deposited on the polymer layer. The metal traces may be oriented substantially along the length of the polymeric insulation. A respective metal trace may be insulated from a second metal trace. The metal traces may also be biocompatible, and can comprise gold or another metal. In an embodiment, the metal traces may comprise another conducting material, and are not limited by the present disclosure. Electrode contacts may be deposited on a side along the length of the biocompatible metal trace. Each electrode contact may be electrically coupled to a respective metal trace. The electrode contacts may also be biocompatible, and can comprise gold or conducting material. A second layer of the polymer may be deposited over the first layer, metal traces, and electrode contacts. An exposed portion of a respective electrode contact may be left to protrude beyond a top edge of the insulated wire defined by a top and a side along the length of the insulated wire.

Figure 3:
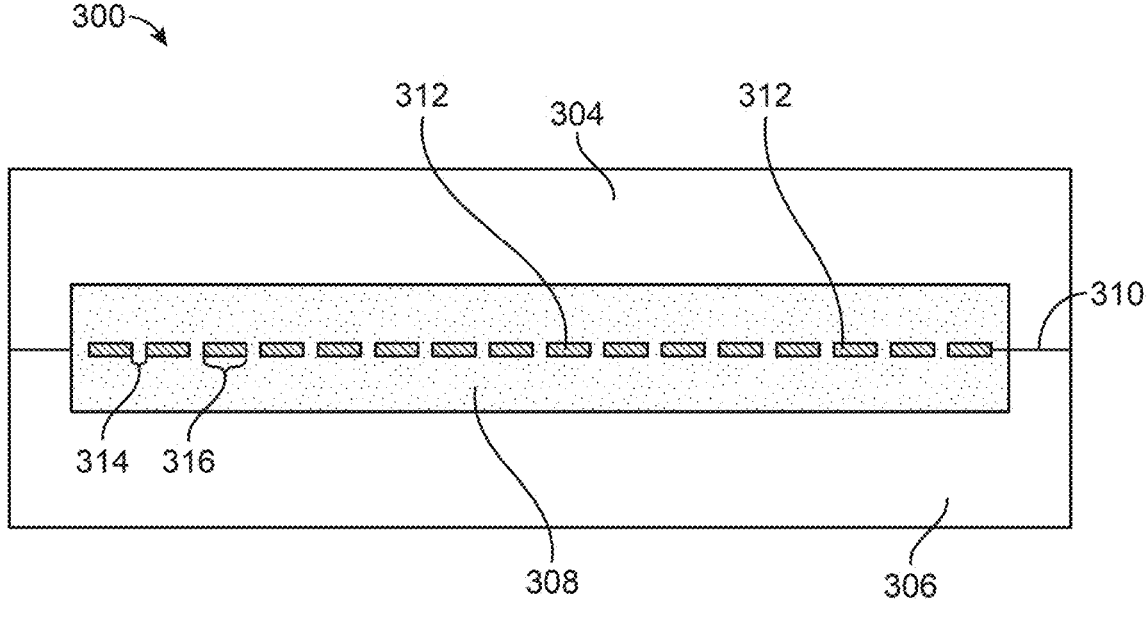
FIG. 3 illustrates another view of a PCTFE enclosure with insulated wires, according to an aspect of the present disclosure.

FIG. 3 illustrates another close-up cross-sectional view of a PCTFE enclosure 300 with insulated wires, according to an aspect of the present disclosure. The PCTFE enclosure 300 includes a first PCTFE portion 304 and a second PCTFE portion 306. The PCTFE portions 304 and 306 are fused together and around a plurality of insulated wires 308. A welded seam 310 joins the PCTFE portions 304 and 306 together between each of the insulated wires 308.

Disposed within each of the wires 308 is a set of metal traces 312. The metal traces 312 are individual metallic threads within the insulation (e.g., each insulated wire 308 is made up of insulation surrounding multiple long metallic strands). The metal traces 312 may include metals and/or metal alloys, including nickel, gold, platinum, platinum alloys, etc. For example, the electrical traces may include a thin gold film.

In some implementations, each of the insulated wires 308 includes 16 metal traces 312. Alternatively, the insulated wires 308 can include any suitable number of metal traces, such as 2, 4, 5, 6, 8, 12, or 32 metal traces. In some embodiments, each of the metal traces is about 2 micrometers (μm) from a neighboring metal trace (distance 314 shown in FIG. 3). The metal traces 312 may be about 2 micrometers (μm) in cross sectional width (distance 316 shown in FIG. 3).

In some embodiments, each of the metal traces 312 terminates in an electrode. The metal traces may have one end within the enclosure 300 and another end with an electrode. The electrode may be configured to send and/or receive signals to/from tissue, such as brain tissue. In some embodiments, the electrode is implanted in a brain. Within the enclosure, in some implementations, the metal traces 312 are connected to circuitry. For example, the implantable device includes a volume disposed between the first portion of the enclosure and the second portion of the enclosure. Sealed within the volume is circuitry which may include one or more integrated circuits. The implantable device may further include, sealed within the volume of the enclosure, communications components such as a wireless communication device, and power components such as a wireless charging device. An example of an implantable device with such components is illustrated and described in further detail in U.S. patent application Ser. No. 16/926,420, "Brain Implant with Subcutaneous Wireless Relay and External Wearable Communication and Power Device," which is incorporated by reference herein in its entirety.

Figure 4:
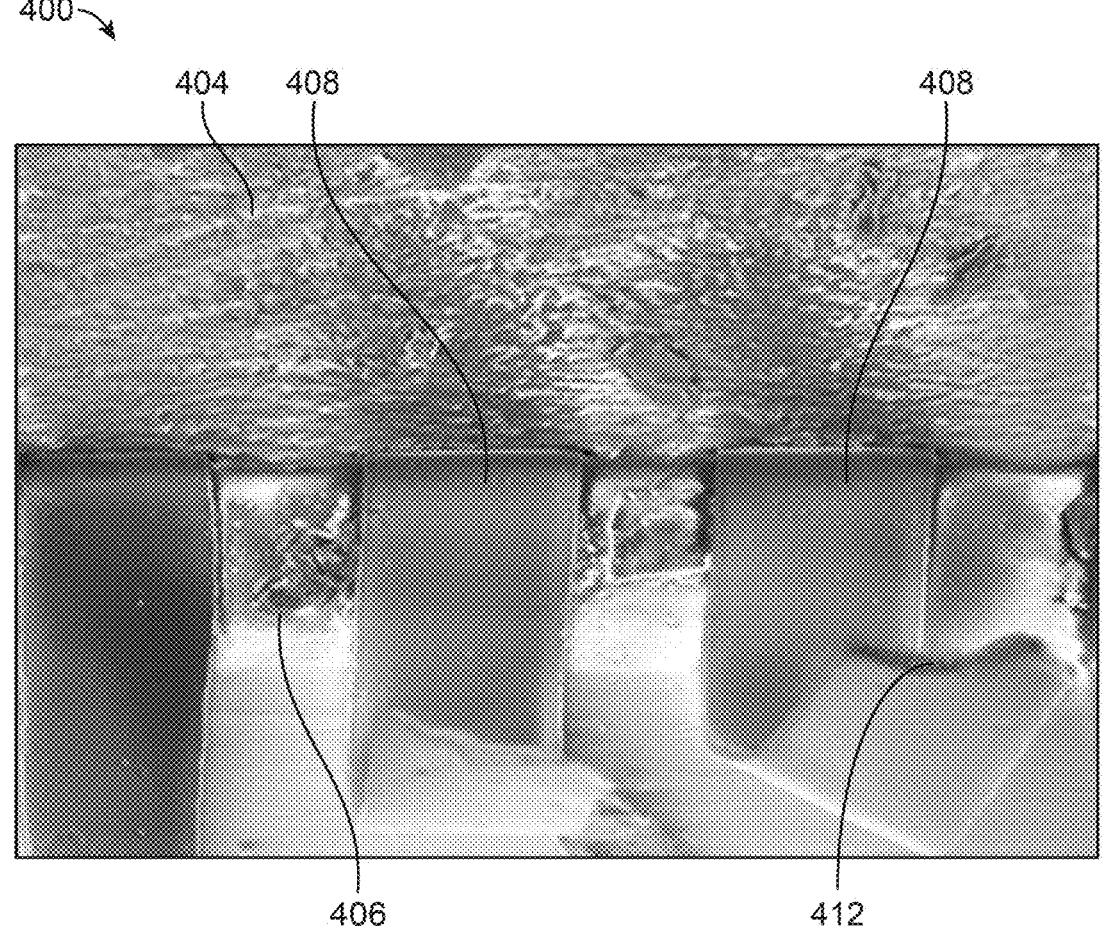
FIG. 4 illustrates another view of a PCTFE enclosure with insulated wires, according to an aspect of the present disclosure.

FIG. 4 illustrates a closer view of a PCTFE enclosure 400 with insulated wires, according to an aspect of the present disclosure. The PCTFE enclosure 400 includes a first PCTFE portion 404, a second PCTFE portion 406, and insulated wires 408 fused between the PCTFE portions 404 and 406. The PCTFE enclosure 400 includes multiple insulated wires 408, each including multiple metal traces 412, as described above with respect to FIG. 3. As shown in FIG. 4, the seal between the PCTFE portions 404 and 406 and around the insulated wires 408 forms a highly integrated interdigitated tack weld of PCTFE surrounding the insulated wires 408.

Figure 5:
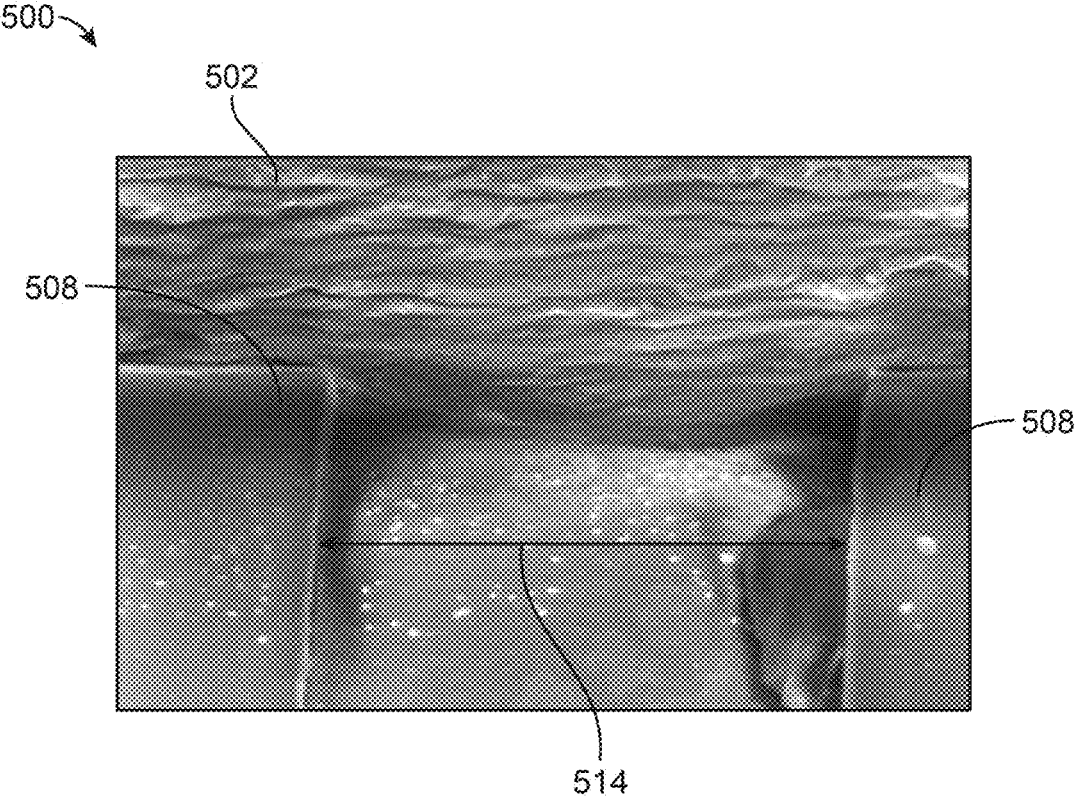
FIG. 5 illustrates another view of a PCTFE enclosure with insulated wires, according to an aspect of the present disclosure.

FIG. 5 illustrates another view of a PCTFE enclosure 500 with insulated wires, according to an aspect of the present disclosure. The wires 508 are spaced apart by a distance 514. In some implementations, the distance 514 is on the order of micrometers (μm). In some embodiments, each wire is separated by less than 150 micrometers (μm) from a neighboring wire of the plurality of insulated wires. For example, the wires are spaced apart by 125 μm, 100 μm, 50 μm, 40 μm, 30 μm, 25 μm, or 20 μm. In some embodiments, each wire of the plurality of insulated wires is separated by between 10 micrometers (μm) and 50 micrometers (μm) from a neighboring wire.

Figure 6:
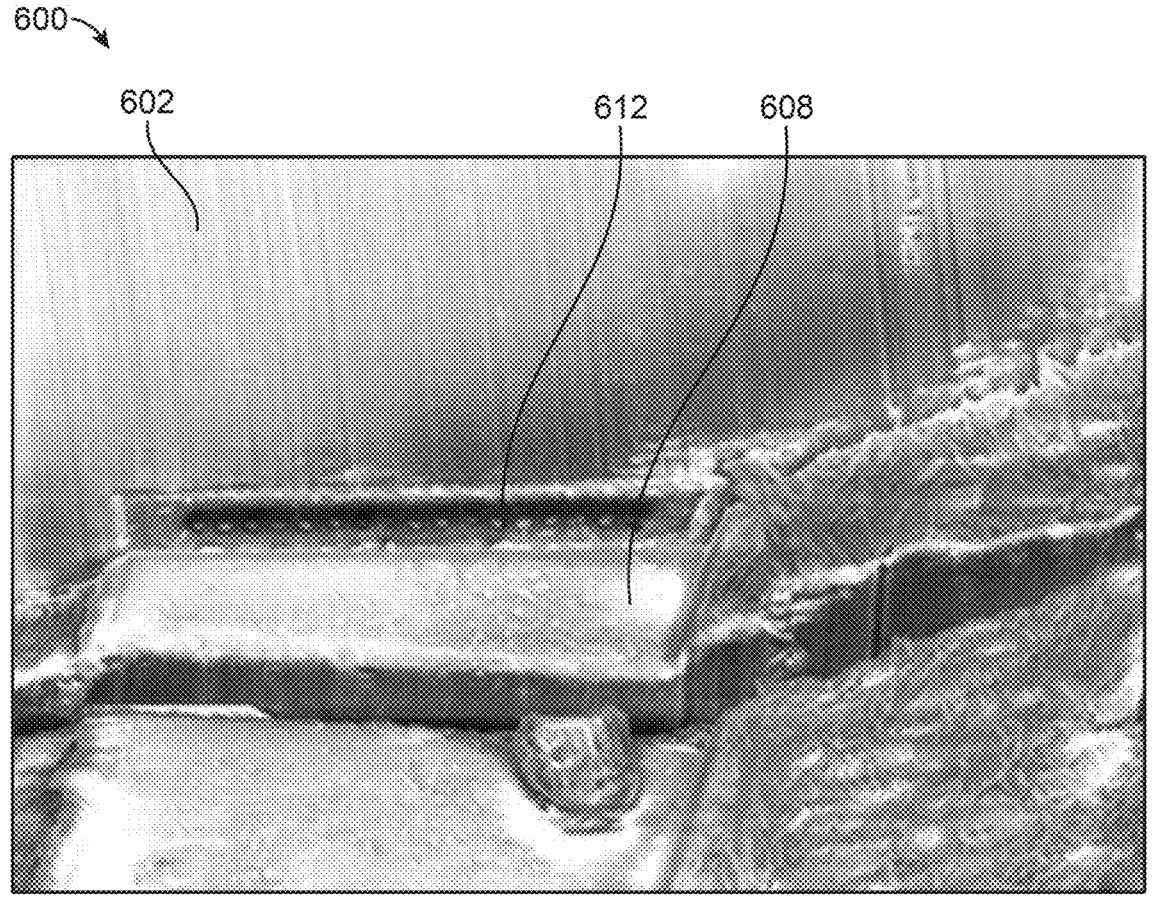
FIG. 6 illustrates another view of a PCTFE enclosure with insulated wires, according to an aspect of the present disclosure.

FIG. 6 illustrates another view of a PCTFE enclosure 600 with insulated wires, according to an aspect of the present disclosure. This is an even closer zoomed-in version of the enclosure and an insulated wire. FIG. 6 shows the PCTFE enclosure 600 fused to an insulated wire 608. Multiple metal traces 612 run through the insulated wire 608, shown in cross-section. FIG. 6 shows a highly integrated interdigitated welded seam of PCTFE surrounding the insulated wire.

Manufacturing a Device with Pctfe Enclosure

Figure 7:
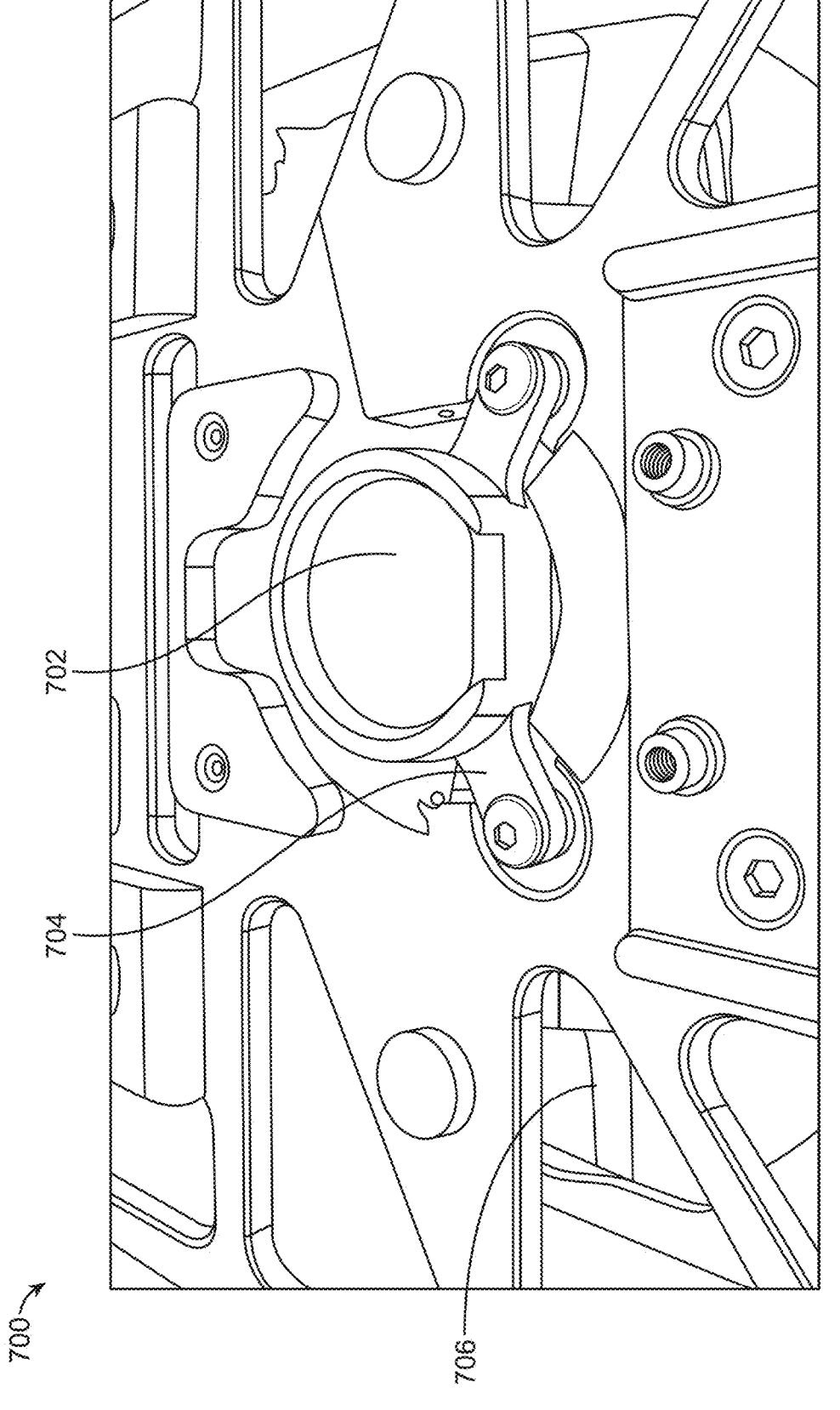
FIG. 7 illustrates a sealing system for manufacturing a PCTFE enclosure, according to an aspect of the present disclosure.

In some embodiments, a PCTFE enclosure as described above with respect to FIGS. 1-6 is manufactured using a sealing system. The sealing system includes components for applying heat and pressure to the portions of the enclosure so as to substantially hermetically seal the PCTFE portions to each other as well as around each of a set of insulated wires spaced apart from one another by a distance on the order of micrometers apart. FIGS. 7-9 illustrate components of such a sealing system.

FIG. 7 illustrates components of a sealing system 700 for manufacturing a PCTFE enclosure, according to an aspect of the present disclosure. The sealing system 700 includes a base 704. The base 704 includes an opening 702. The sealing system 700 further includes a heater 706. The heater 706 may be disposed below the base 704. The heater 706 is configured to apply heat to the PCTFE enclosure for the sealing process. The base 704 may hold the PCTFE enclosure for the sealing process, in some implementations in conjunction with an insert as shown in FIGS. 8A-9.

Figure 8A:
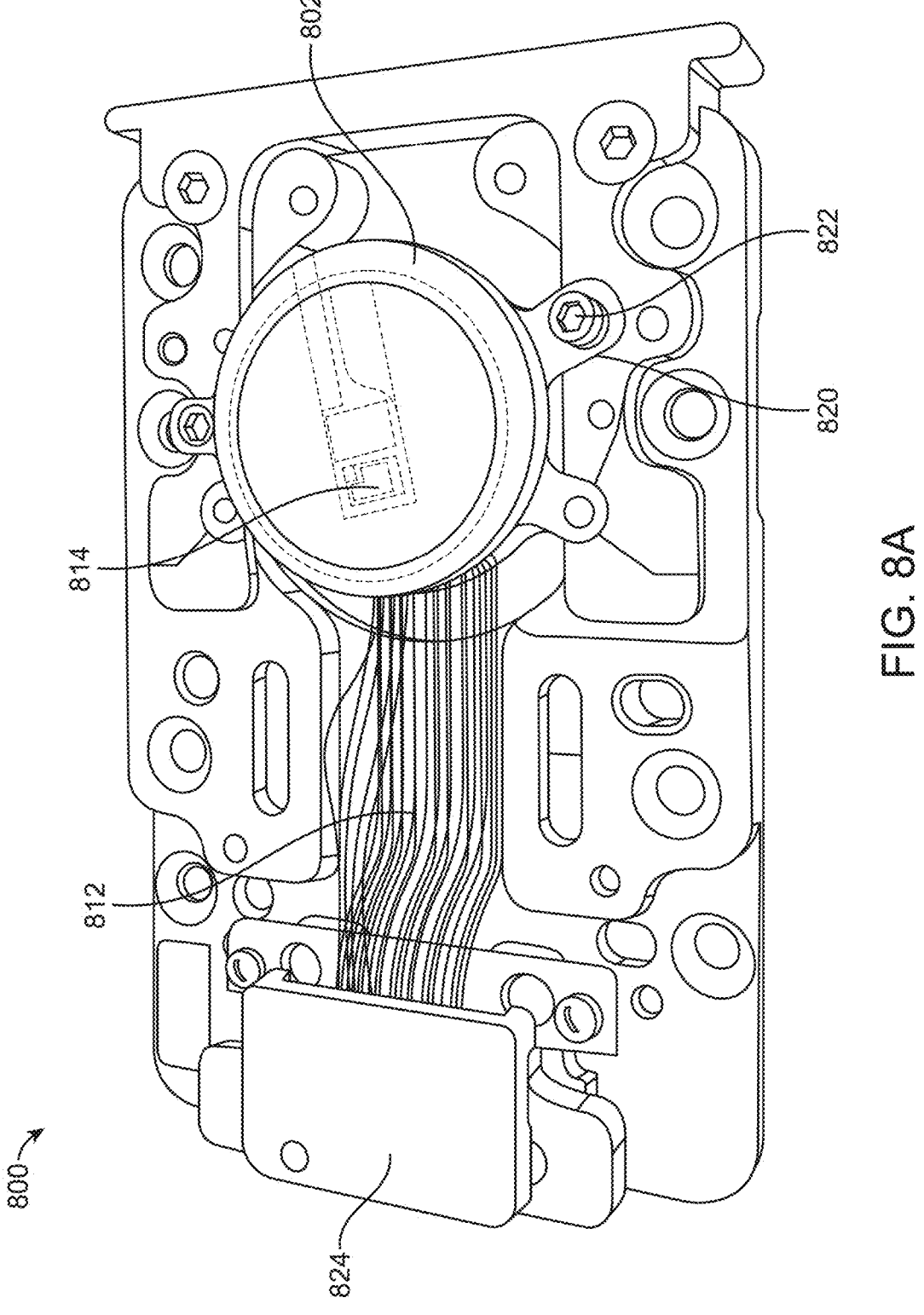
FIG. 8A illustrates a first view of an insert of a sealing system for manufacturing a PCTFE enclosure, according to an aspect of the present disclosure.
Figure 8B:
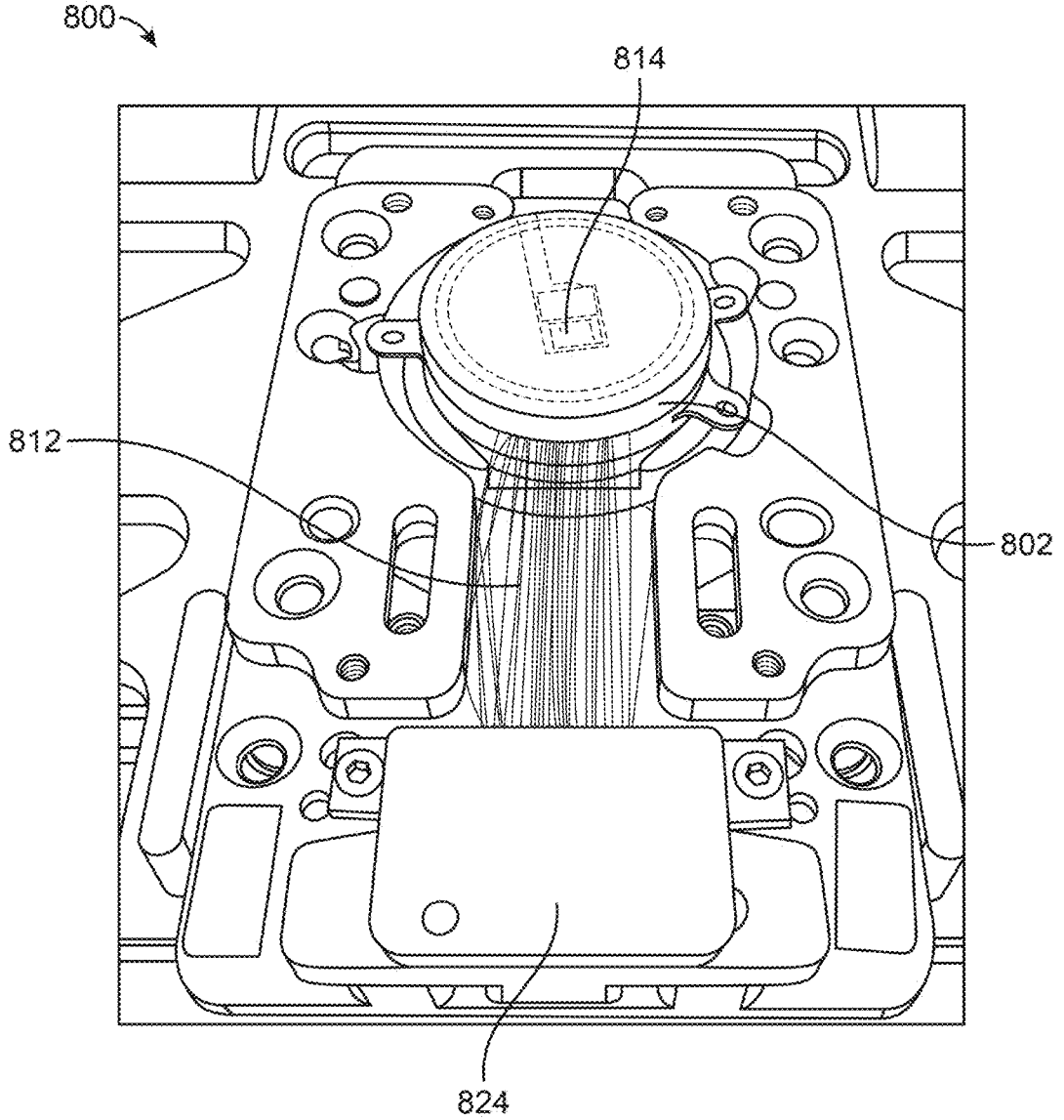
FIG. 8B illustrates a second view of an insert of a sealing system for manufacturing a PCTFE enclosure, according to an aspect of the present disclosure.
Figure 9:
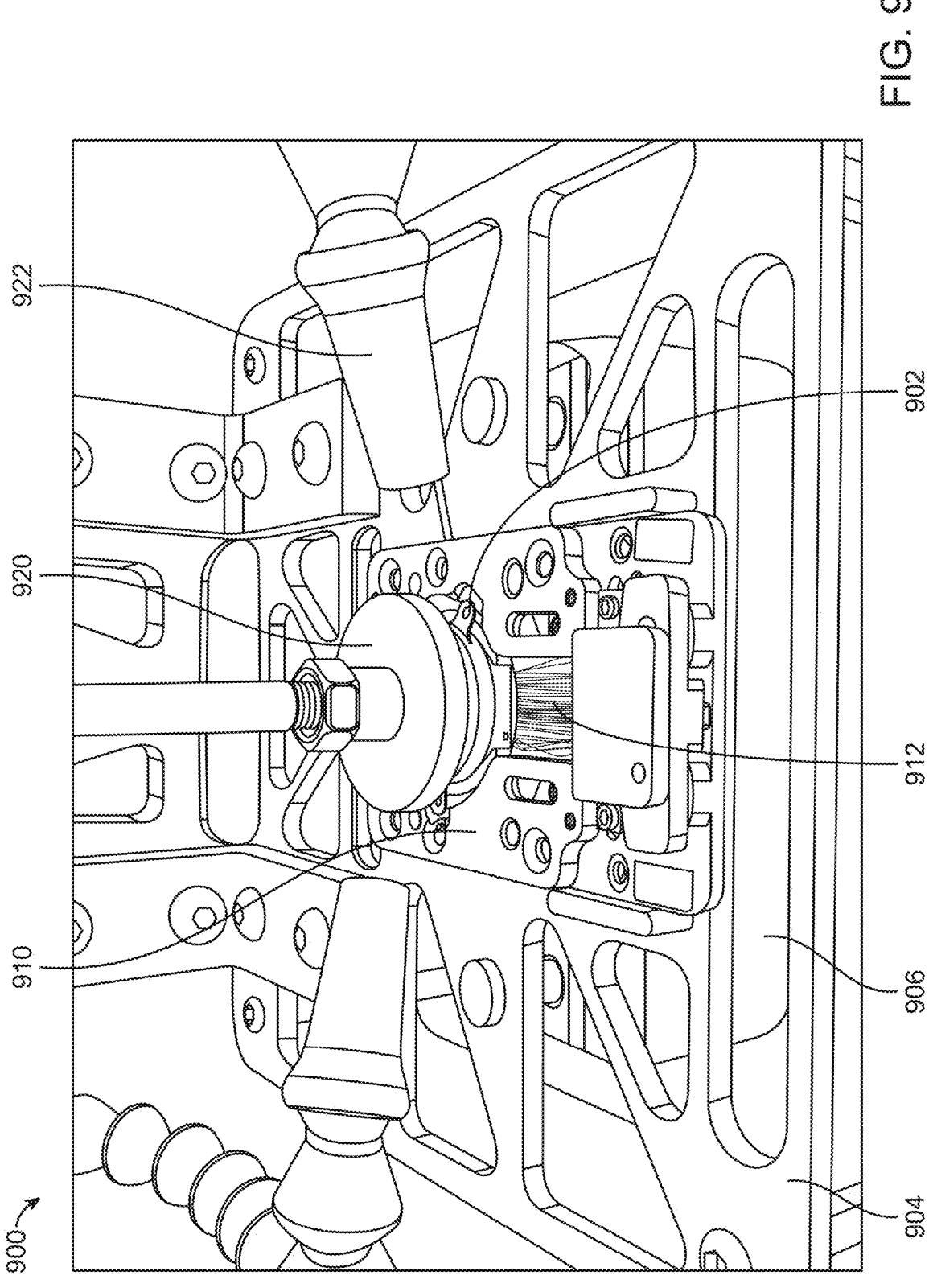
FIG. 9 illustrates a sealing system in operation for manufacturing a PCTFE enclosure, according to an aspect of the present disclosure.

FIGS. 8A and 8B illustrate an insert 800 of a sealing system, according to an aspect of the present disclosure. In some embodiments, the insert 800 is configured to hold a PCTFE enclosure 802 and wires 812 in place during the sealing process. The insert 800 can be disposed in the base 704 shown in FIG. 7 for the sealing process, as depicted in FIG. 9.

As shown in FIGS. 8A and 8B, the PCTFE enclosure 802 is inserted in the insert 800. The PCTFE enclosure 802 includes attachment means 820 in the form of a set of screw holes. The PCTFE enclosure 802 is held tight in the insert 800 via screws 822 screwed in to the attachment means 820. The PCTFE insert 800 holds the PCTFE enclosure 802 firmly in place via the attachment means 820. Alternatively, the PCTFE enclosure 802 can be held in place using other suitable components such as a clamp or a ring.

The insert 800 may include a clamp 824 or other means for holding the wires 812 in place. As shown in FIGS. 8A and 8B, the wires 812 extend out of the PCTFE enclosure 802 so that the wires are flat and lying parallel to one another.

FIGS. 8A and 8B further show circuitry 814 disposed within the enclosure 802. As described above with respect to FIG. 3, the enclosure 802 can be sealed to substantially hermetically enclose components such as circuitry 814. As shown in FIGS. 8A and 8B, the wires 812 are connected to the circuitry 814, and extend out parallel to one another through the enclosure 802.

FIG. 9 illustrates a sealing system 900 for manufacturing a PCTFE enclosure, according to an aspect of the present disclosure. The sealing system includes a base 904, heater 906, and insert 910, as described above with respect to FIGS. 7-8B. The sealing system 900 further includes one or more pistons 920 and air nozzles 922. The implantable device, including PCTFE enclosure 902 and insulated wires 912, is placed in the sealing system 900 for sealing.

The pistons 920 are components configured to apply pressure to the PCTFE enclosure for the sealing process. The pistons 920 may apply pressure by way of hydraulic cylinders, pneumatic cylinders, or other suitable means. In some implementations, the pistons 902 include a first piston (e.g., above the base 904 and insert 910, as depicted in FIG. 9). In some implementations, the pistons further include a second piston, (e.g., below the base 904 and insert 910, not visible in FIG. 9).

As shown in FIG. 9, the enclosure 902 is held in place in the insert 910. The insulated wires 912 extend out of the enclosure 902 and are held in place in the insert 910. Pressure is applied via the pistons 920 and heat is applied via the heater 906. The air nozzles 922 may be configured to apply air to the enclosure 902 during or after the sealing process. For example, after sealing, the air nozzles 922 can be used to cool the enclosure 902. Alternatively, or additionally, the air nozzles 922 can apply cool air to reduce the temperature during the sealing process to keep the temperature applied to the PCTFE portions within a desired range. Under the appropriate temperature and pressure, the PCTFE of the enclosure 902 will melt and reflow around the insulated wires 912, so that the portions of the enclosure 902 fuse with each other and around the insulated wires 912, as further described with respect to FIG. 11.

Figure 10:
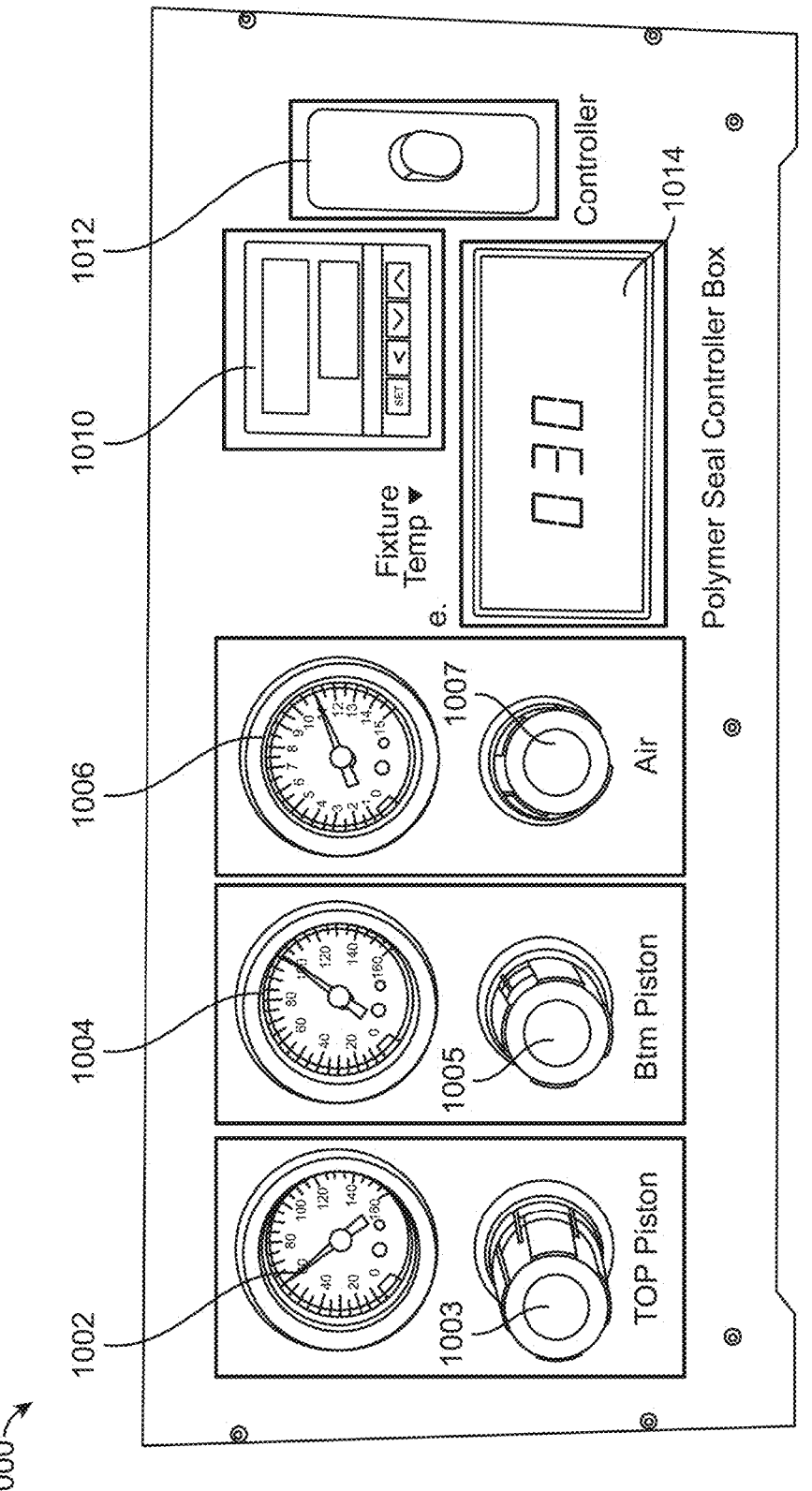
FIG. 10 illustrates a controller for use with the sealing system of FIGS. 8A-9, according to another aspect of the present disclosure.

FIG. 10 illustrates an example of a controller for use with the sealing system of FIGS. 7-9, according to another aspect of the present disclosure. In some implementations, the controller 1000 automatically controls the sealing process.

The controller 1000 includes a pressure gauge 1002 for the top piston, as well as a dial 1003 for an operator to modify the pressure applied by the top piston. The controller 1000 further includes a pressure gauge 1004 for the bottom piston, as well as a dial 1005 for an operator to modify the pressure applied by the bottom piston. The controller 1000 further includes a pressure gauge 1006 for air, as well as a dial 1007 for an operator to modify the pressure applied by the air nozzles.

The controller 1000 includes temperature information and controls. The temperature is shown in a display 1014. Temperature controls 1010 can be interacted with by an operator to modify the temperature of the sealing system.

In some embodiments, based on the configured pressure and temperature settings, the controller 1000 transmits signals to the pistons, the heater, and the air nozzles, as shown in FIGS. 7-9, to maintain the pressure and temperature. For example, the pistons are actuated and the heat produced by the heater is increased or decreased. The controller 1000 can further include a power button 1012 for powering the controller on or off.

Enclosure Manufacture Flow

FIG. 11 is a flowchart illustrating a method 1100 of manufacturing an implantable device, with various steps, or portions thereof, represented in the disclosed flowchart blocks. The manufacturing process includes sealing PCTFE portions of an enclosure so that insulated wires extend out of the enclosure and the enclosure is sealed substantially hermetically. The enclosure may be sealed to protect active electronics such as circuitry, wireless communications systems, power sources, etc. In some implementations, the sealing process is partially or completely automated. A controller of the sealing system may execute instructions to automatically control the temperature, pressure, and timing of the sealing process. The following method is described in the context of PCTFE portions, although other suitable materials such as LCP, HDPE, PTFE, PVDF, PVDC, EVOH, or PAN may also be used.

In some aspects, prior to the sealing process, initial preparations are performed. The initial preparations may include cleaning a PCTFE first portion of the enclosure. For example, the PCTFE first portion is cleaned by sonicating the PCTFE first portion for about 10 minutes in isopropyl alcohol (IPA). The PCTFE first portion may then be heated (e.g., at 80 degrees Celcius (C) for about 10 minutes). The PCTFE second portion also is cleaned. For example, the PCTFE first portion is plasma cleaned using a plasma cleaning machine. Any epoxy residue on the surface of the PCTFE portions of the enclosure may then be trimmed (e.g., using a scalpel). A swab can be used to clean any remaining debris (e.g., a swab wetted with IPA). As shown in FIG. 9, the insert 910 is seated in the base 904. The preparations may further include warming the sealing system. For example, if the sealing system is at a temperature less than some threshold (e.g., 20 degrees C.), then a preheating process is executed to warm up the sealing system above that threshold temperature.

At block 1102, the method can begin with extending insulated wires from within a PCTFE first portion of an enclosure and a PCTFE second portion of the enclosure to outside the enclosure. For example, the PCTFE second portion is provided. The PCTFE second portion may be placed in the sealing system and held in place (e.g., in an insert configured to hold the enclosure, as shown in FIGS. 8A-9). The insulated wires are placed on top of the PCTFE second portion. The PCTFE first portion is placed on top of the PCTFE second portion and the wires, so that the wires extend between the two PCTFE portions. The wires may be adjusted so that they lie straight and parallel to one another at the point of exit of the enclosure, as shown in FIGS. 8A-9.

In some implementations, the base and insert depicted in FIGS. 7-9 are used to arrange the PCTFE portions and the insulated wires. The PCTFE first portion is inserted into an insert disposed in a base. The insulated wires are placed on top of the PCTFE first portion. The insulated wires can be fixed in place (e.g., using a clamp as shown in FIGS. 8A-9). The PCTFE second portion is placed on top of the insulated wires and the PCTFE first portion. The PCTFE portions of the enclosure can be fixed in place to the insert (e.g., using screws as shown in FIGS. 8A-9).

At block 1104, the first and second portions are clamped together so as to squeeze the insulated wires between the PCTFE first and second portions. In some implementations, one or more pistons are applied to one or more of the PCTFE portions to squeeze the PCTFE portions together and thereby squeeze the wires between the PCTFE first and second portions. For example, as illustrated in FIG. 9, pistons can be used to squeeze the wires between the PCTFE first and second portions. In some implementations, the sealing system applies pressure to the PCTFE first portion using a first piston and the sealing system applies pressure to the PCTFE second portion using a second piston. Applying specific pressures to the PCTFE first and second portions can be used to execute a thermocompression sealing process. In some implementations, the pressure applied to the first piston is different from the pressure applied to the second piston. Specifically, in some aspects, the pressure applied to the first piston is between 275,790 Pascals (Pa) (40 pounds per square inch (psi)) and 551,581 Pa (80 psi), e.g., about 413,685 Pa (60 psi), and the pressure applied to the second piston is greater than about 689,476 Pa (100 psi).

Alternatively, or additionally, the sealing system applies a mechanical clamp to the PCTFE first and second portions to squeeze the portions together and thereby squeeze the wires tightly between the PCTFE first and second portions. In such implementations, a clamp can be used to apply pressure to the enclosure portions for thermocompression.

At block 1106, the PCTFE first portion is thermally welded to the PCTFE second portion. In some implementations, the sealing system performs the thermal welding using a heater. As shown in FIGS. 7 and 9, a heater can be disposed below (or in another suitable place nearby) the base in which the implantable device is placed for the sealing process. The heater is activated to heat the PCTFE to its melting point. The PCTFE is heated to at least about 200 degrees C. to melt the PCTFE for the sealing process. The pressure may be applied at 1106 simultaneously to the heating, to execute a thermocompression molding process.

At block 1108, the PCTFE first portion and second portions are thermally melted and adhered around insulation of each and every wire of the insulated wires such that the enclosure is sealed. The sealing system applies heat and pressure to the PCTFE portions of the enclosure. This causes the PCTFE to melt and reflow around the insulated wires. The polymer materials of the PCTFE and the insulation will fuse together and form a seal around each wire. As noted above with respect to block 1106, the PCTFE is heated to at least 200 degrees C. to melt the PCTFE. To avoid the melting of other components of the implantable device, there is an upper limit to the heat that should be applied. For example, PI decomposes at around 400 degrees C. In some implementations, the PCTFE is heated to a temperature between 200 and 300 degrees C. Specifically, the maximum temperature may be set to between 255 C and 260 C. The heater and pistons or other clamping devices may be deactivated after the PCTFE has melted and adhered around the insulation of the insulated wires. The higher the pressure, temperature, and time, the more the PCTFE will melt and flow. The temperature and pressure settings noted above have been found to produce an appropriate amount of reflow without damaging other components of the implantable device, cracking the polymer, or causing too much polymer flow. Too much polymer flow, can, for example, alter the overall profile of the enclosure shape and size.

If other materials are used to form the enclosure in lieu of PCTFE, the temperature range may be adjusted accordingly. For example, LCP can be used at a temperature between 280-335° C., HDPE can be used at a temperature between 120-140° C., PTFE can be used at a temperature between 320-330° C., PVDF can be used at a temperature between 170-180° C. PVDC can be used at a temperature between 163-191° C., EVOH can be used at a temperature between 156-195° C., or PAN can be used at a temperature between 190-240° C.

After the PCTFE portions are melted and adhered, the implantable device may be cooled. For example, after a predetermined time of applying heat and pressure to the PCTFE portions, the sealing system transitions to a cooling mode. The sealing system may monitor the temperature until the implantable device is cooled enough for unloading. The sealing system may notify a user (e.g., with an alarm sound) once cooling is complete. The user can then detach the implantable device from the sealing system (e.g., by unscrewing any screws, unclamping any clamps, etc.).

Example Computer System

Figure 12:
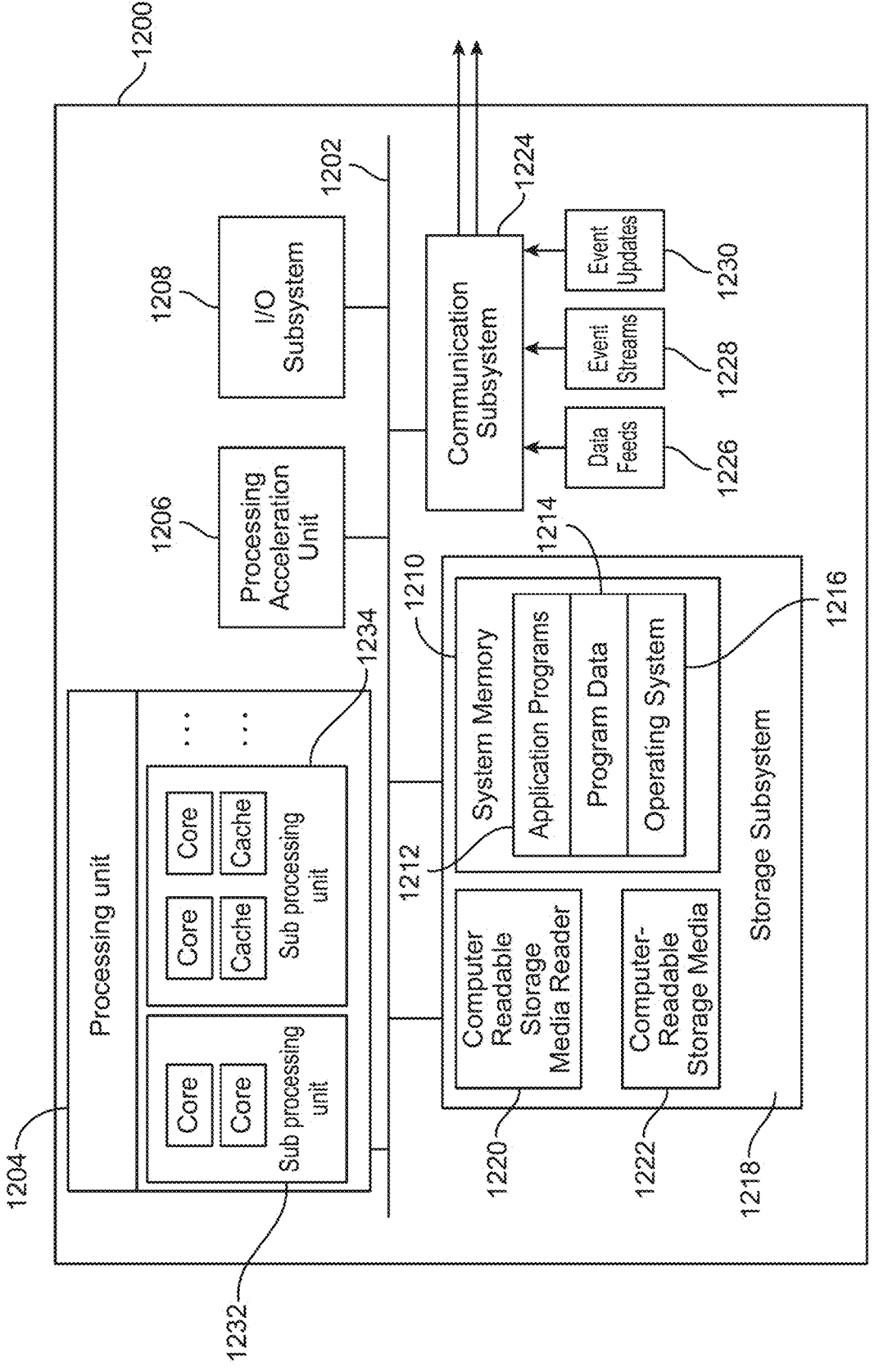
FIG. 12 illustrates an example computer system that may be used to implement certain embodiments.

FIG. 12 illustrates an example computer system 1200 that may be used to implement certain embodiments. For example, in some embodiments, computer system 1200 may be used to implement any of the systems for manufacturing components of an implantable device described above. As shown in FIG. 12, computer system 1200 includes various subsystems including a processing subsystem 1204 that communicates with a number of other subsystems via a bus subsystem 1202. These other subsystems may include a processing acceleration unit 1206, an I/O subsystem 1208, a storage subsystem 1218, and a communications subsystem 1224. Storage subsystem 1218 may include non-transitory computer-readable storage media including storage media 1222 and a system memory 1210.

Bus subsystem 1202 provides a mechanism for letting the various components and subsystems of computer system 1200 communicate with each other as intended. Although bus subsystem 1202 is shown schematically as a single bus, alternative embodiments of the bus subsystem may utilize multiple buses. Bus subsystem 1202 may be any of several types of bus structures including a memory bus or memory controller, a peripheral bus, a local bus using any of a variety of bus architectures, and the like. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard, and the like.

Processing subsystem 1204 controls the operation of computer system 1200 and may comprise one or more processors, application specific integrated circuits (ASICs), or field programmable gate arrays (FPGAs). The processors may include be single core or multicore processors. The processing resources of computer system 1200 can be organized into one or more processing units 1232, 1234, etc. A processing unit may include one or more processors, one or more cores from the same or different processors, a combination of cores and processors, or other combinations of cores and processors. In some embodiments, processing subsystem 1204 can include one or more special purpose co-processors such as graphics processors, digital signal processors (DSPs), or the like. In some embodiments, some or all of the processing units of processing subsystem 1204 can be implemented using customized circuits, such as application specific integrated circuits (ASICs), or field programmable gate arrays (FPGAs).

In some embodiments, the processing units in processing subsystem 1204 can execute instructions stored in system memory 1210 or on computer readable storage media 1222. In various embodiments, the processing units can execute a variety of programs or code instructions and can maintain multiple concurrently executing programs or processes. At any given time, some or all of the program code to be executed can be resident in system memory 1210 and/or on computer-readable storage media 1222 including potentially on one or more storage devices. Through suitable programming, processing subsystem 1204 can provide various functionalities described above. In instances where computer system 1200 is executing one or more virtual machines, one or more processing units may be allocated to each virtual machine.

In certain embodiments, a processing acceleration unit 1206 may optionally be provided for performing customized processing or for off-loading some of the processing performed by processing subsystem 1204 so as to accelerate the overall processing performed by computer system 1200.

I/O subsystem 1208 may include devices and mechanisms for inputting information to computer system 1200 and/or for outputting information from or via computer system 1200. In general, use of the term input device is intended to include all possible types of devices and mechanisms for inputting information to computer system 1200. User interface input devices may include, for example, a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may also include motion sensing and/or gesture recognition devices such as the Microsoft Kinect® motion sensor that enables users to control and interact with an input device, the Microsoft Xbox® 360 game controller, devices that provide an interface for receiving input using gestures and spoken commands. User interface input devices may also include eye gesture recognition devices such as the Google Glass® blink detector that detects eye activity (e.g., "blinking" while taking pictures and/or making a menu selection) from users and transforms the eye gestures as inputs to an input device (e.g., Google Glass®). Additionally, user interface input devices may include voice recognition sensing devices that enable users to interact with voice recognition systems (e.g., Siri® navigator) through voice commands.

Other examples of user interface input devices include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, and medical ultrasonography devices. User interface input devices may also include, for example, audio input devices such as MIDI keyboards, digital musical instruments and the like.

In general, use of the term output device is intended to include all possible types of devices and mechanisms for outputting information from computer system 1200 to a user or other computer. User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. For example, user interface output devices may include, without limitation, a variety of display devices that visually convey text, graphics and audio/video information such as monitors, printers, speakers, headphones, automotive navigation systems, plotters, voice output devices, and modems.

Storage subsystem 1218 provides a repository or data store for storing information and data that is used by computer system 1200. Storage subsystem 1218 provides a tangible non-transitory computer-readable storage medium for storing the basic programming and data constructs that provide the functionality of some embodiments. Storage subsystem 1218 may store software (e.g., programs, code modules, instructions) that when executed by processing subsystem 1204 provides the functionality described above. The software may be executed by one or more processing units of processing subsystem 1204. Storage subsystem 1218 may also provide a repository for storing data used in accordance with the teachings of this disclosure.

Storage subsystem 1218 may include one or more non-transitory memory devices, including volatile and non-volatile memory devices. As shown in FIG. 12, storage subsystem 1218 includes a system memory 1210 and a computer-readable storage media 1222. System memory 1210 may include a number of memories including a volatile main random access memory (RAM) for storage of instructions and data during program execution and a non-volatile read only memory (ROM) or flash memory in which fixed instructions are stored. In some implementations, a basic input/output system (BIOS), containing the basic routines that help to transfer information between elements within computer system 1200, such as during start-up, may typically be stored in the ROM. The RAM typically contains data and/or program modules that are presently being operated and executed by processing subsystem 1204. In some implementations, system memory 1210 may include multiple different types of memory, such as static random access memory (SRAM), dynamic random access memory (DRAM), and the like.

By way of example, and not limitation, as depicted in FIG. 12, system memory 1210 may load application programs 1212 that are being executed, which may include various applications such as Web browsers, mid-tier applications, relational database management systems (RDBMS), etc., program data 1214, and an operating system 1216. By way of example, operating system 1216 may include various versions of Microsoft Windows®, Apple Macintosh®, and/or Linux operating systems, a variety of commerciallyavailable UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, Palm® OS operating systems, and others.

Computer-readable storage media 1222 may store programming and data constructs that provide the functionality of some embodiments. Computer-readable media 1222 may provide storage of computer-readable instructions, data structures, program modules, and other data for computer system 1200. Software (programs, code modules, instructions) that, when executed by processing subsystem 1204 provides the functionality described above, may be stored in storage subsystem 1218. By way of example, computer-readable storage media 1222 may include non-volatile memory such as a hard disk drive, a magnetic disk drive, an optical disk drive such as a CD ROM, DVD, a Blu-Ray® disk, or other optical media. Computer-readable storage media 1222 may include, but is not limited to, Zip® drives, flash memory cards, universal serial bus (USB) flash drives, secure digital (SD) cards, DVD disks, digital video tape, and the like. Computer-readable storage media 1222 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs.

In certain embodiments, storage subsystem 1218 may also include a computer-readable storage media reader 1220 that can further be connected to computer-readable storage media 1222. Reader 1220 may receive and be configured to read data from a memory device such as a disk, a flash drive, etc.

In certain embodiments, computer system 1200 may support virtualization technologies, including but not limited to virtualization of processing and memory resources. For example, computer system 1200 may provide support for executing one or more virtual machines. In certain embodiments, computer system 1200 may execute a program such as a hypervisor that facilitated the configuring and managing of the virtual machines. Each virtual machine may be allocated memory, compute (e.g., processors, cores), I/O, and networking resources. Each virtual machine generally runs independently of the other virtual machines. A virtual machine typically runs its own operating system, which may be the same as or different from the operating systems executed by other virtual machines executed by computer system 1200. Accordingly, multiple operating systems may potentially be run concurrently by computer system 1200.

Communications subsystem 1224 provides an interface to other computer systems and networks. Communications subsystem 1224 serves as an interface for receiving data from and transmitting data to other systems from computer system 1200. For example, communications subsystem 1224 may enable computer system 1200 to establish a communication channel to one or more client devices via the Internet for receiving and sending information from and to the client devices. For example, the communication subsystem may be used to receive speech input from a client device and send a value to the client device in response.

Communication subsystem 1224 may support both wired and/or wireless communication protocols. For example, in certain embodiments, communications subsystem 1224 may include radio frequency (RF) transceiver components for accessing wireless voice and/or data networks (e.g., using cellular telephone technology, advanced data network technology, such as 3G, 4G or EDGE (enhanced data rates for global evolution), Wi-Fi (IEEE 802.XX family standards, or other mobile communication technologies, or any combination thereof), global positioning system (GPS) receiver components, and/or other components. In some embodiments communications subsystem 1224 can provide wired network connectivity (e.g., Ethernet) in addition to or instead of a wireless interface.

Communication subsystem 1224 can receive and transmit data in various forms. For example, in some embodiments, in addition to other forms, communications subsystem 1224 may receive input communications in the form of structured and/or unstructured data feeds 1226, event streams 1228, event updates 1230, and the like. For example, communications subsystem 1224 may be configured to receive (or send) data feeds 1226 in real-time from users of social media networks and/or other communication services such as Twitter® feeds, Facebook® updates, web feeds such as Rich Site Summary (RSS) feeds, and/or real-time updates from one or more third party information sources.

In certain embodiments, communications subsystem 1224 may be configured to receive data in the form of continuous data streams, which may include event streams 1228 of real-time events and/or event updates 1230, that may be continuous or unbounded in nature with no explicit end. Examples of applications that generate continuous data may include, for example, sensor data applications, financial tickers, network performance measuring tools (e.g. network monitoring and traffic management applications), click-stream analysis tools, automobile traffic monitoring, and the like.

Communications subsystem 1224 may also be configured to communicate data from computer system 1200 to other computer systems or networks. The data may be communicated in various different forms such as structured and/or unstructured data feeds 1226, event streams 1228, event updates 1230, and the like to one or more databases that may be in communication with one or more streaming data source computers coupled to computer system 1200.

Computer system 1200 can be one of various types, including a handheld portable device (e.g., an iPhone® cellular phone, an iPad® computing tablet, a PDA), a wearable device (e.g., a Google Glass® head mounted display), a personal computer, a workstation, a mainframe, a kiosk, a server rack, or any other data processing system. Due to the ever-changing nature of computers and networks, the description of computer system 1200 depicted in FIG. 12 is intended only as a specific example. Many other configurations having more or fewer components than the system depicted in FIG. 12 are possible. Based on the disclosure and teachings provided herein, a person of ordinary skill in the art will appreciate other ways and/or methods to implement the various embodiments.

It should be appreciated that the robotic system handling, coupling with, and engaging with one or more portions of a probe device can include a control system (or microprocessor controller) having one or more microprocessors/processing devices that can further be a component of the overall system. The control system can be local or remote to the robotic system, and can also include a display interface and/or operational controls configured to be handled by a user to alter the program of the robotic arm, to visualize the probe device, to visualize biological tissue into which the probe device is being inserted, and change configurations of the robotic device, and sub-portions thereof. Such processing devices can be communicatively coupled to a non-volatile memory device via a bus. The non-volatile memory device may include any type of memory device that retains stored information when powered off. Non-limiting examples of the memory device include electrically erasable programmable read-only memory ("ROM"), flash memory, or any other type of non-volatile memory. In some aspects, at least some of the memory device can include a non-transitory medium or memory device from which the processing device can read instructions. A non-transitory computer-readable medium can include electronic, optical, magnetic, or other storage devices capable of providing the processing device with computer-readable instructions or other program code. Non-limiting examples of a non-transitory computer-readable medium include (but are not limited to) magnetic disk(s), memory chip(s), ROM, random-access memory ("RAM"), an ASIC, a configured processor, optical storage, and/or any other medium from which a computer processor can read instructions. The instructions may include processor-specific instructions generated by a compiler and/or an interpreter from code written in any suitable computer-programming language, including, for example, C, C++, C#, Java, Python, Perl, JavaScript, etc.

While the above description describes various embodiments of the invention and the best mode contemplated, regardless how detailed the above text, the invention can be practiced in many ways. Details of the system may vary considerably in its specific implementation, while still being encompassed by the present disclosure. As noted above, particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific examples disclosed in the specification, unless the above Detailed Description section explicitly defines such terms. Accordingly, the actual scope of the invention encompasses not only the disclosed examples, but also all equivalent ways of practicing or implementing the invention under the claims.

The teachings of the invention provided herein can be applied to other systems, not necessarily the system described above. The elements and acts of the various examples described above can be combined to provide further implementations of the invention. Some alternative implementations of the invention may include not only additional elements to those implementations noted above, but also may include fewer elements. Further any specific numbers noted herein are only examples; alternative implementations may employ differing values or ranges, and can accommodate various increments and gradients of values within and at the boundaries of such ranges.

References throughout the foregoing description to features, advantages, or similar language do not imply that all of the features and advantages that may be realized with the present technology should be or are in any single embodiment of the invention. Rather, language referring to the features and advantages is understood to mean that a specific feature, advantage, or characteristic described in connection with an embodiment is included in at least one embodiment of the present technology. Thus, discussion of the features and advantages, and similar language, throughout this specification may, but do not necessarily, refer to the same embodiment. Furthermore, the described features, advantages, and characteristics of the present technology may be combined in any suitable manner in one or more embodiments. One skilled in the relevant art will recognize that the present technology can be practiced without one or more of the specific features or advantages of a particular embodiment. In other instances, additional features and advantages may be recognized in certain embodiments that may not be present in all embodiments of the present technology.

What is claimed is:

1. An implantable device comprising:

a polychlorotrifluoroethylene (PCTFE) first portion of an enclosure;

a PCTFE second portion of the enclosure, the first and second portions configured to mate with each other to form the enclosure;

a plurality of insulated wires, each wire of the plurality of insulated wires parallel to each other and separated by less than 150 micrometers (um) from a neighboring wire of the plurality of insulated wires, the plurality of insulated wires extending between the first and second portions of the enclosure; and a thermal weld seam of PCTFE disposed between the first portion of the enclosure and the second portion of the enclosure to join the first portion and the second portion, the thermal weld seam of PCTFE conformally adhering around insulation of each and every wire of the plurality of insulated wires such that the enclosure is sealed.

2. The implantable device of claim 1, wherein:

the insulation of each of the plurality of insulated wires is composed of polyimide.

3. The implantable device of claim 1, wherein:

each wire of the plurality of insulated wires has a rectangular cross section, having been produced by lithography.

4. The implantable device of claim 1, wherein:

the plurality of insulated wires comprises at least 500 wires.

5. The implantable device of claim 1, wherein:

each wire of the plurality of insulated wires includes a plurality of metal traces terminating in a respective plurality of electrodes.

6. The implantable device of claim 5, wherein:

each wire of the plurality of insulated wires is separated by between 10 micrometers ($\mu$m) and 50 micrometers ($\mu$m) from a neighboring wire.

7. The implantable device of claim 5, wherein:

the electrodes are configured to be implanted in a brain.

8. The implantable device of claim 1, further comprising:

a volume disposed between the first portion of the enclosure and the second portion of the enclosure; and an integrated circuit sealed within the volume.

9. The implantable device of claim 1, further comprising:

a volume disposed between the first portion of the enclosure and the second portion of the enclosure; and a wireless charging device sealed within the volume.

10. The implantable device of claim 1, wherein:

each wire of the plurality of insulated wires includes a plurality of metal traces terminating in a respective plurality of electrodes, and each of the plurality of metal traces is 2 $\mu$m from a neighboring metal trace.

11. The implantable device of claim 10, wherein:

each of the plurality of metal traces is 2 $\mu$m in cross-sectional width.

12. The implantable device of claim 1, wherein:

the insulation of each of the plurality of insulated wires is composed of polyimide, each wire of the plurality of insulated wires has a rectangular cross section, having been produced by lithography, the plurality of insulated wires comprises at least 500 wires, each wire of the plurality of insulated wires includes a plurality of metal traces terminating in a respective plurality of electrodes, and each wire of the plurality of insulated wires is separated by between 10 micrometers ($\mu$m) and 50 micrometers ($\mu$m) from a neighboring wire.

13. The implantable device of claim 1, wherein:

the insulation of each of the plurality of insulated wires is composed of polyimide, each wire of the plurality of insulated wires has a rectangular cross section, having been produced by lithography, the plurality of insulated wires comprises at least 500 wires, each wire of the plurality of insulated wires includes a plurality of metal traces terminating in a respective plurality of electrodes, each wire of the plurality of insulated wires is separated by between 10 micrometers ($\mu$m) and 50 micrometers ($\mu$m) from a neighboring wire, and the electrodes are configured to be implanted in a brain.

14. The implantable device of claim 1, further comprising:

a volume disposed between the first portion of the enclosure and the second portion of the enclosure; and an integrated circuit sealed within the volume, wherein:

the insulation of each of the plurality of insulated wires is composed of polyimide, each wire of the plurality of insulated wires has a rectangular cross section, having been produced by lithography, the plurality of insulated wires comprises at least 500 wires, each wire of the plurality of insulated wires includes a plurality of metal traces terminating in a respective plurality of electrodes, each wire of the plurality of insulated wires is separated by between 10 micrometers ($\mu$m) and 50 micrometers ($\mu$m) from a neighboring wire, and the electrodes are configured to be implanted in a brain.

* * * * *